United States Patent
Roukes et al.

(10) Patent No.: US 6,722,200 B2
(45) Date of Patent: Apr. 20, 2004

(54) APPARATUS AND METHOD FOR ULTRASENSITIVE NANOELECTROMECHANICAL MASS DETECTION

(75) Inventors: Michael L. Roukes, Pasadena, CA (US); Kamil L. Ekinci, Brookline, MA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/138,538

(22) Filed: May 3, 2002

(65) Prior Publication Data

US 2003/0033876 A1 Feb. 20, 2003

Related U.S. Application Data

(60) Provisional application No. 60/288,741, filed on May 4, 2001.

(51) Int. Cl.⁷ .......................... G01N 11/00; G01G 3/14; G01L 1/10
(52) U.S. Cl. .................. 73/580; 73/54.41; 73/32 A; 73/504.16; 73/504.12
(58) Field of Search ................ 73/54.41, 32 A, 73/579, 580, 504.12, 504.16; 310/316.01, 311, 312

(56) References Cited

U.S. PATENT DOCUMENTS

| | | | |
|---|---|---|---|
| 4,905,701 A | 3/1990 | Cornelius | |
| 5,201,215 A | 4/1993 | Granstaff et al. | |
| 5,914,553 A | 6/1999 | Adams et al. | |
| 6,326,563 B1 | 12/2001 | Takeuchi et al. | |
| 6,389,877 B1 * | 5/2002 | Takeuchi et al. | 73/19.03 |
| 6,457,360 B1 * | 10/2002 | Daraktchiev et al. | 73/579 |
| 6,457,361 B1 * | 10/2002 | Takeuchi et al. | 73/580 |

* cited by examiner

Primary Examiner—Hezron Williams
Assistant Examiner—Rose M. Miller
(74) Attorney, Agent, or Firm—Daniel L. Dawes; Myers Dawes Andras & Sherman LLP (57) ABSTRACT

The invention relates to the application of the techniques of nanoelectromechanical systems (NEMS) to ultrasensitive mass detection. A pulsed flux of atoms is adsorbed onto the surface of a 32.8 MHz nanomechanical resonator within an ultrahigh vacuum environment. The mass-induced frequency shifts from these adsorbates are then used to demonstrate a mass sensitivity of $\sim 1.46 \times 10^6$ Daltons (Da). For resonators operating up to frequencies of 72 MHz, inverse mass responsivities as small as $\sim 8 \times 10^{-20}$ grams/Hz ($5 \times 10^4$ Da/Hz) are obtained. Our results offer a new approach to ultrahigh resolution mass spectrometry of individual, electrically-neutral macromolecules with clear prospects for single Dalton sensitivity.

25 Claims, 6 Drawing Sheets

APPARATUS AND METHOD FOR ULTRASENSITIVE NANOELECTROMECHANICAL MASS DETECTION

RELATED APPLICATIONS

The present application is related to U.S. Provisional Patent Application serial No. 60/288,741 filed on May 4, 2001 to which priority is claimed under 35 USC 119 and which is incorporated herein by reference.

GOVERNMENT RIGHTS

The U.S. Government has certain rights in this invention pursuant to Grant No. DABT63-98-1-0012 awarded by DARPA.

BACKGROUND OF THE INVENTION

1. Field of the Invention

The invention relates to the application of the techniques of nanoelectromechanical systems (NEMS) to ultrasensitive mass detection.

2. Description of the Prior Art

Micro-Electro-Mechanical Systems (MEMS) is the integration of mechanical elements, sensors, actuators, and electronics on a common silicon substrate through the utilization of microfabrication technology. While the electronics are fabricated using integrated circuit (IC) process sequences (e.g., CMOS, Bipolar, or BICMOS processes), the micromechanical components are fabricated using compatible "micromachining" processes that selectively etch away parts of the silicon wafer or add new structural layers to form the mechanical and electromechanical devices.

MEMS promises to revolutionize nearly every product category by bringing together silicon-based microelectronics with micromachining technology, thereby, making possible the realization of complete systems-on-a-chip. MEMS technology makes possible the integration of microelectronics with active perception and control functions, thereby, expanding the design and application space.

Whereas MEMS devices and processes are typically in the range of 1 to 100 microns, nanotechnologies contemplates processes a thousand times smaller, approaching a size just above or at the size of large molecules. Nanotechnologies thus contemplate processes and objects, which tend to be more chemical in nature than microelectronic. However, the availability of MEMS devices raises the question of whether these devices can be used in any advantageous way to measure and perform tasks at the next scale of size down, name in the 1 to 100's of molecules or atoms. Such technologies are by analogy referred to as nanoelectromechanical systems (NEMS).

What is needed then is an apparatus and method by which such nano-processes can be accessed.

BRIEF SUMMARY OF THE INVENTION

The invention is defined as a method for measuring microscopic magnitudes of mass and an apparatus realizing such a measurement, thereby enabling a novel approach to mass spectrometry. The method involves driving a nanoelectromechanical resonator at its resonance frequency, attaching the mass to be determined to the resonator by means of a chemical or physical adsorption process, and detecting changes in this resonance frequency due to the mass added to the vibrating element.

The apparatus further comprises a vacuum chamber for enclosing the nanoelectromechanical resonator and for directing the adsorbate molecules onto the resonator. The added mass is of the order of one or more macromolecules of matter adsorbed onto the vibrating element. Ideally, the added mass may be as small as one Dalton.

In the illustrated embodiment the vibrating element comprises a doubly clamped SiC beam. However, it is to be expressly understood that any nanoelectromechanical resonator now known or later devised is considered as an equivalent for the purposes of the invention. For example, torsional resonators, compound resonators with more than one vibrating element or arrays of resonators are other types of nanoelectromechanical devices which may be used.

In the illustrated embodiment vibrating element comprises a VHF microelectromechanical element. The higher the frequency, the better sensitivity is obtained.

The illustrated embodiment also comprises a plurality of baffles to shield the nanoelectromechanical resonator from radiation and includes means for thermally shielding or stabilizing the nanoelectromechanical resonator, such as a cryogenic bath surrounding the nanoelectromechanical resonator and thermally coupled thereto.

The apparatus can detect an added mass $$\delta M \sim C \frac{M_{tot}}{Q} 10^{-(DR/20)},$$

where $\delta M$ is the minimal magnitude of mass measurable by the nanoelectromechanical resonator, C is a constant determined by the geometry of the vibrating element, $M_{tot}$ is the total mass of the vibrating element, Q is the resonant quality factor of the nanoelectromechanical resonator, and DR is the dynamic range of the nanoelectromechanical resonator and the measurement circuit. The added mass consists substantially of uncharged matter adsorbed to the vibrating element.

The invention is also defined as a method comprised of the steps of using the above defined apparatus to measure microscopic added masses to a nanoelectromechanical resonator.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Microelectromechanical systems (MEMS) and, more recently, nanoelectromechanical systems (NEMS) have found a host of applications in semiconductor-based technology and fundamental science. The present invention demonstrates that NEMS also open important new prospects for mass spectrometry, a ubiquitous experimental research tool that has enabled scores of scientific breakthroughs in the period since its origins more than 90 years ago.

Given their extremely small masses, high frequency NEMS resonators are exquisitely sensitive to added mass. In the present work we demonstrate that this attribute makes it feasible to observe the adsorption of individual macromolecules onto the surface of a nanomechanical device. Furthermore, we believe that it is technically feasible to resolve the mass of individual adsorbed molecules with single-Dalton (Da) resolution. To provide a concrete initial demonstration of this ultimate potential for "weighing" individual molecules, we herein disclose studies of the response of nanometer scale VHF mechanical resonators to a gated, ballistic flux of atoms.

Figure 1A:
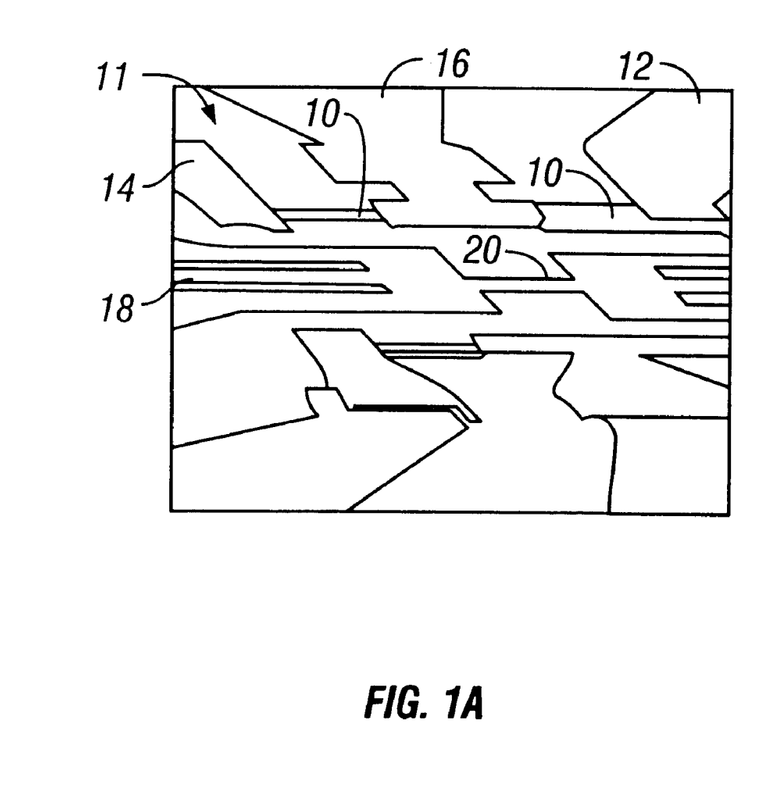
FIGS. 1a and 1b are microphotographs of a nanomechanical resonators used for ultrasensitive mass detection.
Figure 1B:
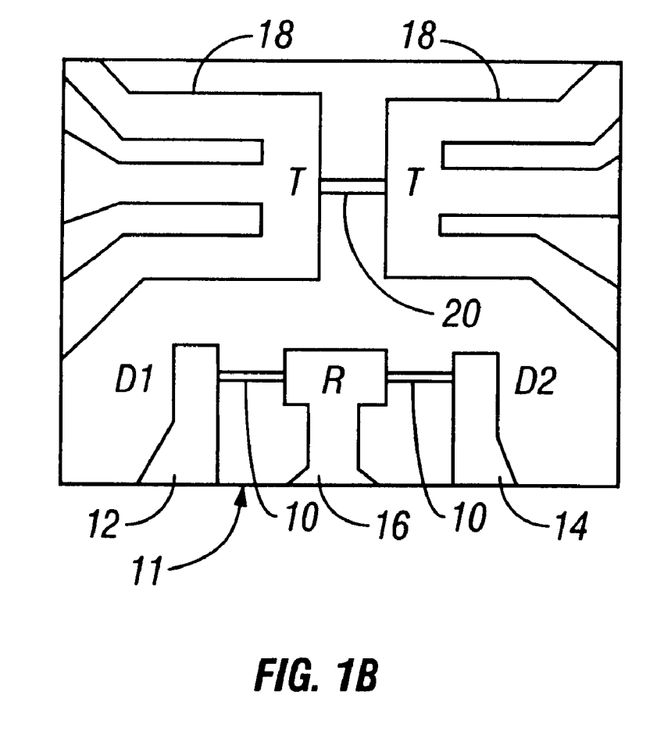

In these experiments, the fundamental-mode resonance frequency of a doubly-clamped silicon carbide (SiC) beam, such as the one pictured in FIGS. 1a and 1b, is tracked continuously by a phase-locked loop (PLL) circuit. FIGS. 1a and 1b are microphotographs of a nanomechanical resonators used for ultrasensitive mass detection. The top surface of all beams 10 are metallized with, 80 nm of Al or 6 nm/40 nmCr/Au. The vibrating element or beam 10 is placed in a magnetic field and an alternating current is driven across the thin metal electrode on top of the beam. This subjects the beam to a fluctuating Lorentz Force at the drive frequency. The drive frequency is then adjusted so as to match mechanical resonance frequency of the beam, thereby causing it to vibrate as a damped harmonic oscillator. The displacements of the beam are sensed by detecting the electromotive force generated on the metal electrodes due the motion of the beam. Pairs of doubly-clamped SiC beams 10, located in the background in the perspective view of FIG. 1a on the lower portion of the plan view of FIG. 1b constitute three-port RF bridges. Electrode/anchor pads 12 and 14, also labeled D1 (Drive 1), D2 (Drive 2) are driven out-of-phase to yield a virtual ground at the R (readout) electrode 16. This results in significant background suppression of the static part of the beam impedance. The central structure 18, also labeled T, enables four-wire resistance measurements of the local temperature of an equivalent, suspended beam 20 co-fabricated with those employed for the mass measurement (cf. FIG. 5).

Figure 2:
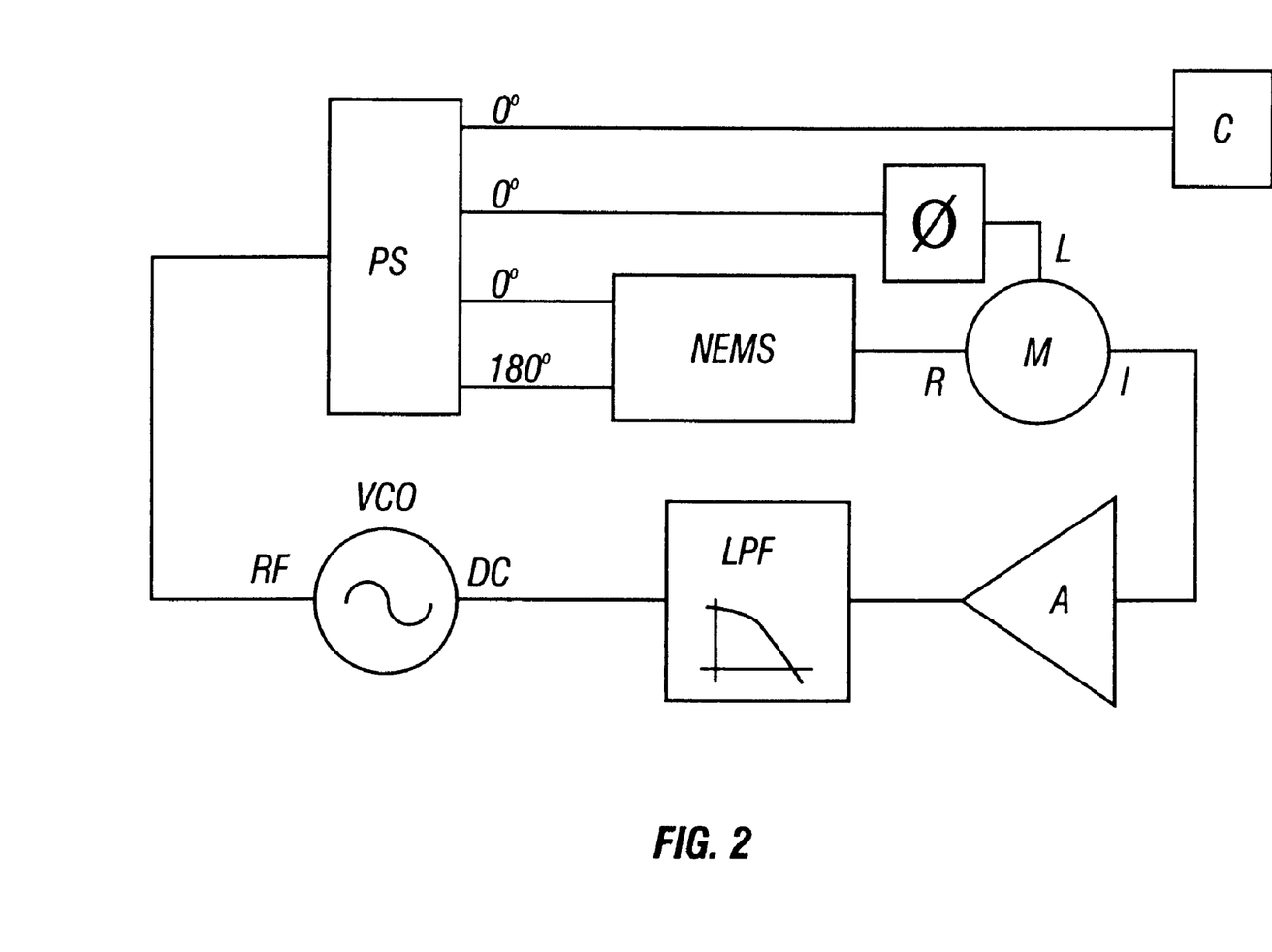
FIG. 2 is a conceptual diagram of the phase-locked loop NEMS readout used in the illustrated embodiment.

The electronic instrumentation is schematically depicted in FIG. 2, wherein a conceptual diagram of the phase-locked loop NEMS readout used in the illustrated embodiment is shown. The principal components are: (VCO) voltage controlled RF oscillator 22; (PS) 4-port power splitter 24 with three 0° and one 180° output ports; (NEMS) high frequency nanoelectromechanical mass sensor 26 with an RF bridge readout; (M) mixer 28 where R, L and I are the RF, LO and IF ports respectively; (Ø) phase shifter 30; (A) variable gain amplifier 32; (LPF) low pass filter 34; and (C) frequency counter 36. The counter 36 is connected to a digital computer 38 for data acquisition. The nanoelectromechanical resonators configured in an RF bridge as shown in FIG. 1 serve as the mass sensor 26 in the electronic measurement circuit. The operation of the foregoing electronics is briefly described as follows: The nanoelectromechanical resonator 11 is driven at its mechanical resonance frequency by taking advantage of the feedback loop of the circuit of FIG. 2. The VCO 22 supplies the drive signal, the electromotive force generated on the resonator 11 due to its motion is then mixed with this drive signal by mixer 28, amplified by amplifier 32 and low pass filtered filtered by filter 34. The output of the LPF 34 constitutes the error signal which is used as the (quasi) DC signal to operate the VCO 22. As the mechanical resonance frequency of the resonator 11 changes, the error signal changes, thereby tracking the resonance frequency.

Figure 3:
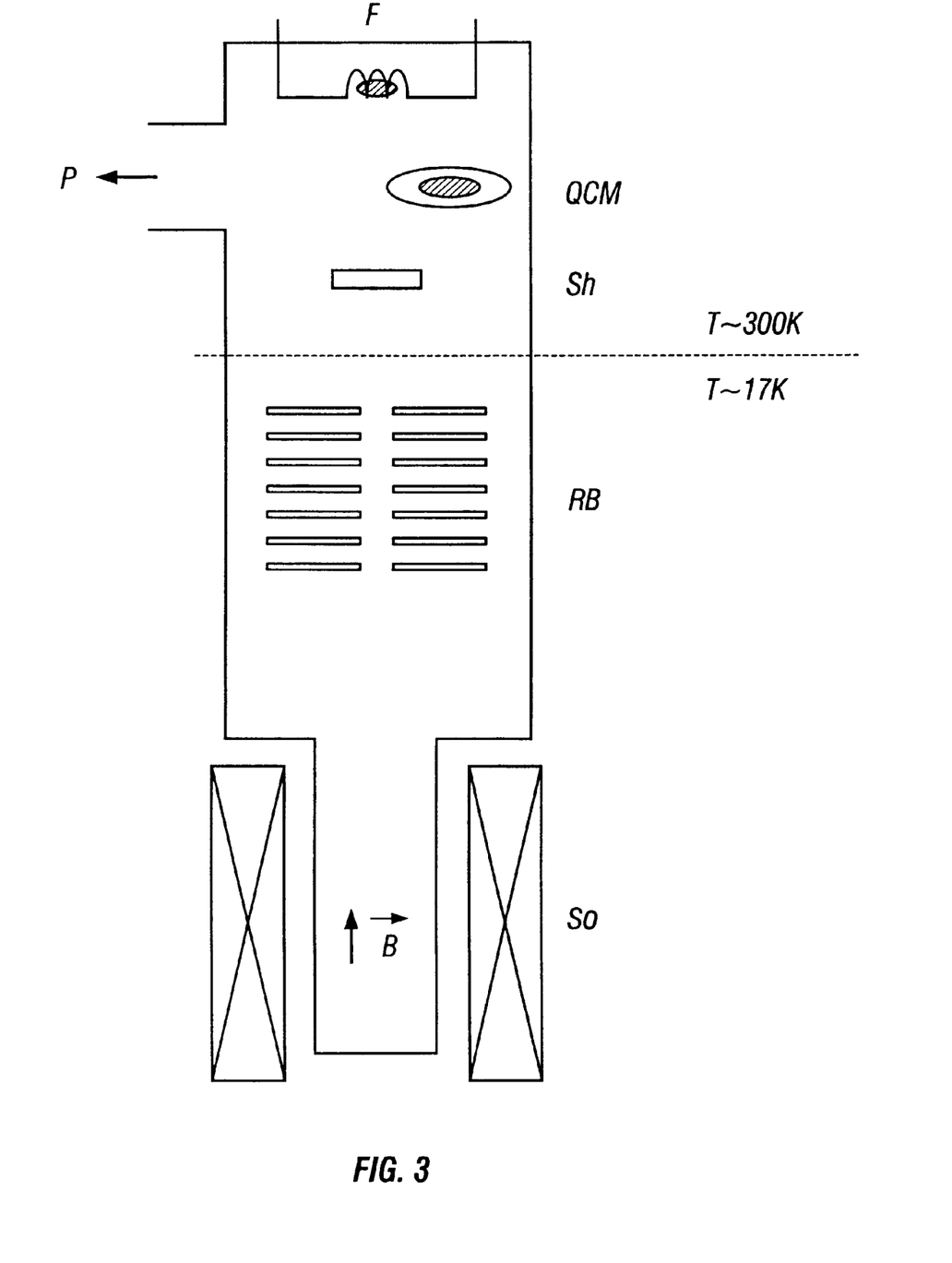
FIG. 3 is a block diagram of the UHV microwave cryostat used in the demonstration of the illustrated embodiment.

These experiments are carried out under UHV conditions within the apparatus depicted in FIG. 3. FIG. 3 is a block diagram of the UHV microwave cryostat 40 used in the demonstration of the illustrated embodiment. The mass sensitivity measurements are done in a variable temperature, ultra-high vacuum (UHV) cryostat 40 enabling high frequency measurements (<30 GHz) upon NEMS of FIGS. 1a and 1b. The sample chamber 42 is inserted into the bore 44 of a 6T superconducting solenoid 46 (So) immersed in liquid helium (not shown). Prior to insertion in the helium bath, turbo and ion pumps 48 (P) evacuate the system 40 to $10^{-9}$ Torr range. Once inside the helium bath, we estimate that the sample chamber pressure drops below $\sim 10^{-10}$ Torr. The radiation baffles 50 (RB) attached to the low temperature end of the cryostat 40 establish a line of sight from a room temperature thermal-evaporation source 52 (F) of Au atoms to the bottom of the cryostat 40. Measurements of the mass sensitivity of NEMS beams or resonators 11 are carried out by carefully placing them in this line-of-sight, 182.2 cm away from the thermal-evaporation source 52. A calibrated quartz crystal resonator 54 (QCM) at a distance of 13.3 cm and a room temperature shutter 56 (Sh) are employed to determine and regulate the flux. The thickness of the material deposited upon the NEMS devices 11 is determined, assuming uniform coverage, from this flux value and the surface area of the device 11 as measured by electron microscopy. During these experiments the sample temperature is regulated at approximately 17 K. At this low temperature, an adsorbate sticking probability of unity is achieved. This temperature also allows a careful monitoring of the resonator temperature (see FIG. 5). This system permits us to direct an extremely weak, ballistic, flux of atoms onto the surface of a NEMS device. Using a 32.8 MHz nanomechanical resonator 11, the instrumentation and apparatus yield a noise floor for mass measurement, for a 2 ms averaging time. Devices 11 with fundamental-mode resonances at 72 MHz have provided even better inverse responsivity, yielding values approaching $2\pi$ ($\delta M/\partial \omega$) or about $5 \times 10^4$ Da/Hz.

Figure 4:
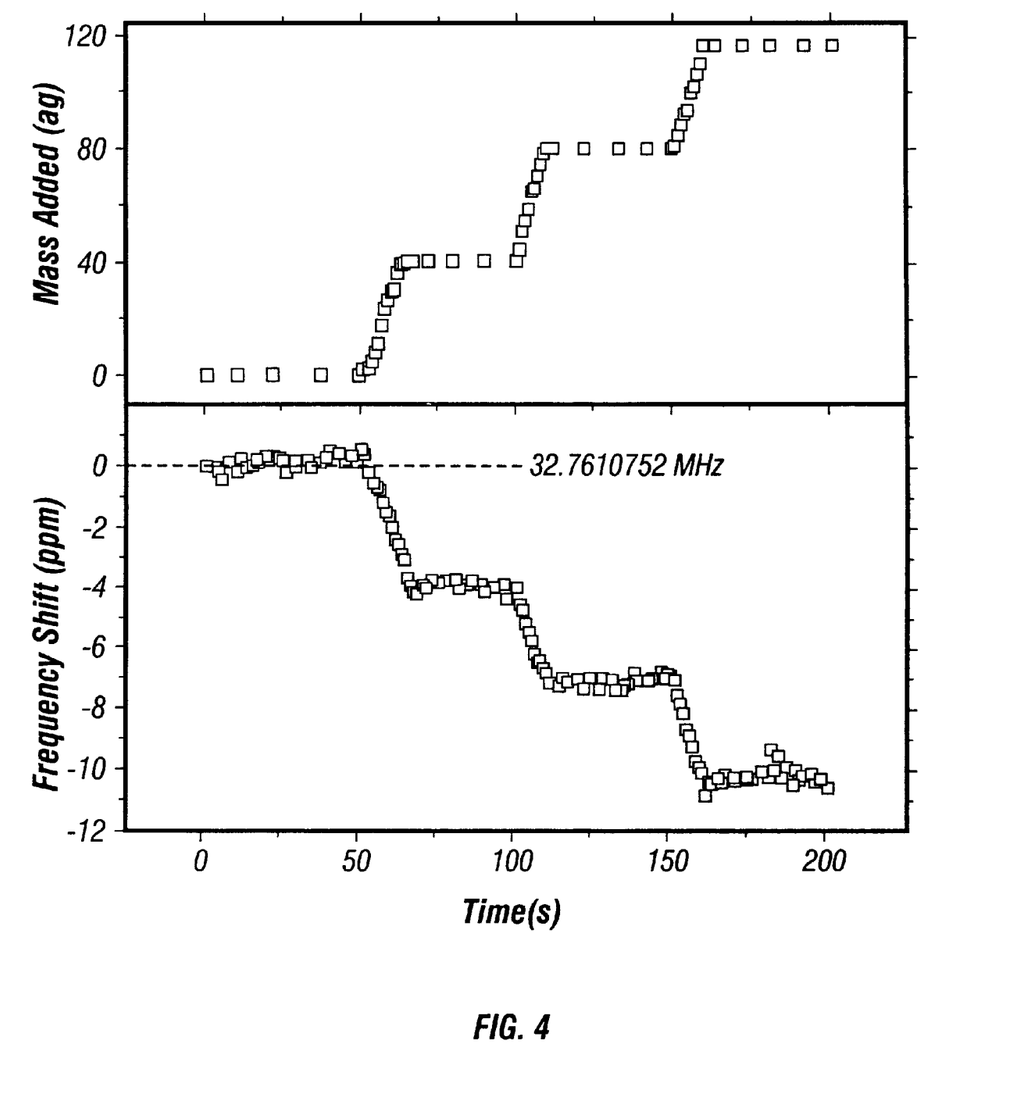
FIG. 4 is a graph of the massed added and the frequency shifts as a function of time induced by gold atom adsorption upon a 0.67 $\mu$m×0.259 $\mu$m×14.2 $\mu$m SiC doubly-clamped beam with (initial) fundamental frequency ~32.8 MHz as followed by a phase-locked loop.

In FIG. 4 we display the temporal evolution of the resonant frequency of a SiC beam ($f_0^{initial}$ about 32.8 MHz) exposed to a ballistic flux of Au atoms. FIG. 4 is a graph of the massed added and the frequency shifts as a function of time induced by gold atom adsorption upon a 0.67 $\mu m \times 0.259~\mu m \times 14.2~\mu m$ SiC doubly-clamped beam with (initial) fundamental frequency ~32.8 MHz as followed by a phase-locked loop. A constant flux of thermally evaporated Au atoms was established before the shutter 56 was opened between designated times. The inverse mass responsivity, $$\frac{\partial M_{eff}}{\partial \omega_0}$$

is determined from the steps in the plot. The noise floor of the measurement is determined from the regions of constant frequency when the shutter 56 was closed. For this experiment, a measurement bandwidth of $\Delta f=3$ kHz (T ~2 ms) yielded a noise floor of 6.51 Hz and corresponds to a minimum detectable mass $\delta M=7400~m_{AU}=1.46\times10^6$ Da, here $m_{Au}$ is the mass of a Au atom. Adsorption commences when shutter 56, placed directly between the resonator 11 and the Au source 52, is opened during specific time intervals. The data illustrate that the experimental noise floor for mass detection, measured in the absence of the atomic flux, is set by the 6.51 Hz (rms) frequency fluctuations at the detection system's output. Again, for the 32.8 MHz device employed here, this corresponds to a mass sensitivity of $1.46\times10^6$ Da (rms). We have taken special precautions in these measurements, given that the NEMS resonator 11 will be exposed to both hot incoming atoms and blackbody radiation from the thermal source 52. These could potentially generate spurious fluctuations and drift in the temperature of the mechanical resonator 11, and thereby compromise its frequency stability. This is of special concern here, given that the thermal conductance between a suspended NEMS device 11 and its environment (which governs the thermalization rate) can be exceptionally small. Given that the mechanical resonance frequency exhibits finite temperature dependence, this could directly translate to fluctuations and undesired shifts in operating frequency. FIG. 5 demonstrates that we have suppressed these phenomena in our experiments.

Figure 5A:
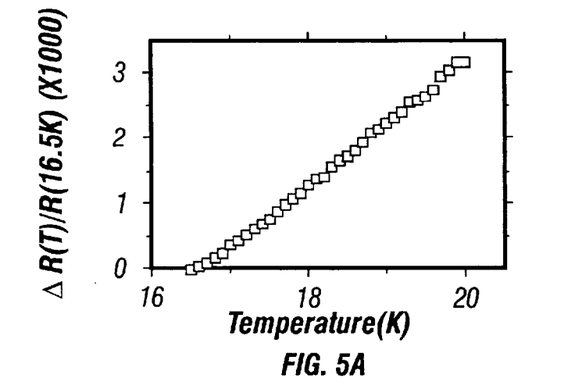
FIGS. 5a, 5b and 5c are graphs of the four-probe electrical measurements of the device resistance while the resonator is exposed to atom fluxes comparable to those employed in our experiments.
Figure 5B:
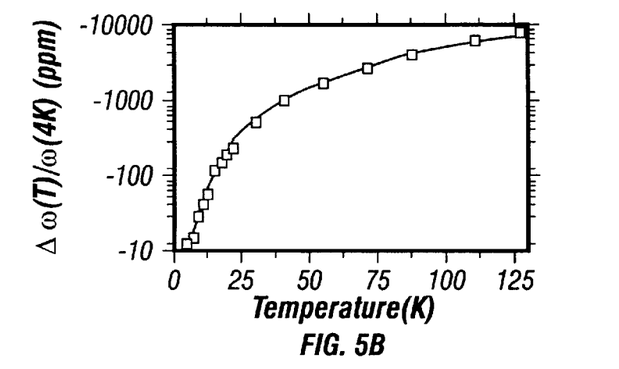
Figure 5C:
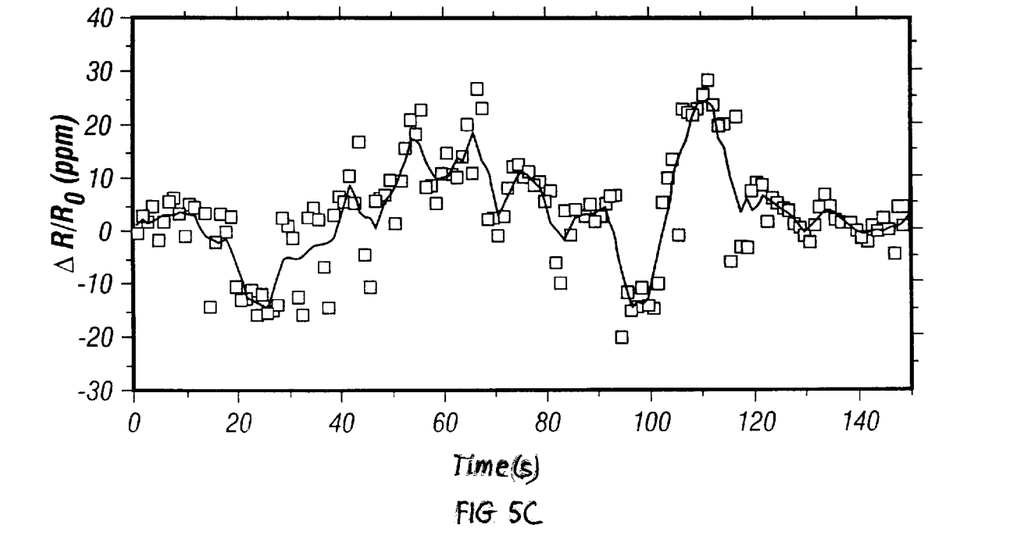

FIGS. 5a, 5b and 5c are graphs of the four-probe electrical measurements of the device resistance while the resonator is exposed to atom fluxes comparable to those employed in our experiments. FIG. 5c shows the temporal evolution of the resistance fluctuations $\Delta R/R_0$ before and during exposure to the atom flux. The shutter 56 was opened at t=50 and left open. The resistance fluctuations, $\Delta R/R_0$ of the metal electrode are converted to temperature fluctuations using measured values of temperature dependence of the four-terminal resistance, $\partial R(T)/\partial T$, obtained from the same beam 10 in the vicinity of T=17 K as shown in FIG. 5a. Separate measurements of the temperature dependence of the resonance frequency in this regime, $\partial f_0(T)/\partial T$ then allow estimation of the thermally induced frequency shift $\delta f_0 = \{[\partial f_0(T)/\partial T]/[\partial R(T)/\partial T]\}\delta R$. The frequency fluctuations thus deduced are found to be about 10 Hz, comparable to our noise floor for zero flux, hence no significant effect is observed for the very low fluxes employed in these experiments. The average Au thickness deposited on the beam during the course of the measurement was less than $4\times10^{-3}$ nm.

We now explore the level of performance that should become possible for optimized, next-generation NEMS mass sensors. To provide a realistic estimate, we first write the mass sensitivity as $$\delta M \approx \frac{\partial M_{eff}}{\partial \omega_0}\delta\omega_0 = \frac{1}{R}\delta\omega_0 \qquad [1]$$

Here $\delta\omega_0$ is the minimum resolvable frequency shift and $R=\partial\omega_0/\partial M_{eff}$ is defined as the mass responsivity.

To evaluate this expression we proceed as follows. The vibratory mass of the resonator is mode-specific, and is defined by the ratio $M_{eff}=K_{eff}/\omega_0^2$ where $K_{eff}=\beta Ew(t/l)^3$ the effective force constant for the given mode and $\omega_0=2\pi\alpha(E/\rho)^{1/2}(t/l^2)$ is the mode's angular frequency. where w is the width of the beam, E is the elastic modulus of the beam, $\rho$ is mass density of the beam, t is thickness of the beam, and l is length of the beam. For a doubly-clamped beam (cantilever) vibrating in its fundamental mode, $\alpha=1.05$ (0.1615) and $\beta=32$ (0.67), hence $M_{eff}=\beta/(4\pi^2\alpha^2)\sim0.735 M_{tot}$ ($0.65=M_{tot}$) Here $M_{tot}$ is the total mass of the resonator.

The responsivity is then $$R = \frac{\partial\omega_0}{\partial M_{eff}} = \frac{1}{2\omega_0}\frac{\partial(\omega_0^2)}{\partial M_{eff}} = -\frac{1}{2}\frac{\omega_0}{M_{eff}} \qquad [2]$$

hence, $$\delta M \approx -2M_{eff}\frac{\delta\omega_0}{\omega_0} \qquad [3]$$

To make further progress, we must establish the minimum resolvable frequency shift, $\delta\omega_0$. As a rough estimate, we first consider the mass loading required to shift the resonance by its half width, i.e. to obtain $\delta\omega_0 \sim \Delta\omega = \omega_0/Q\delta\omega_0 \sim$ In this case we find, $$\delta M \sim -2\frac{\beta}{\alpha^2}\frac{M_{tot}}{Q} \qquad [4]$$

This first-pass crude analysis serves to illustrate an important point that remains true in the more detailed analyses that follow: the mass sensitivity is proportional to the ratio of the vibratory mass divided by its Q, the quality factor of the resonator. Hence, small, high quality factor resonators are optimal for mass detection. This illustrates the potential impact that nanoscale devices can offer for mass sensing applications. The sensitivity of a NEMS resonator to added mass can apparently be a very small fraction of its total mass if its Q is high.

To obtain a better estimate we should write the minimum resolvable frequency as $$\partial M_{eff}/\partial\omega_0 \simeq -1.47 M_{tot}/\omega_0\delta\omega_0 \sim [S_f^{(eff)}\Delta f]^{\frac{1}{2}} = [(S_f^i + S_f^{(RO)})\Delta f]^{\frac{1}{2}} \qquad [5]$$

Here $\Delta f \sim 2\pi/\tau$ is the effective bandwidth, which depends upon the measurement averaging time, $\tau$; and $S_f^{eff}$ is the effective spectral density of the frequency fluctuations. The latter is comprised of processes intrinsically linked to the resonator itself (e.g. its phase noise and long term drift), as well as those introduced from the readout process. We shall denote these noise spectral densities $S_f^i$ and $S_f^{(RO)}$, respectively. In practice a resonator's frequency fluctuations depend upon its materials properties, geometry, and the experimental conditions (e.g. temperature, pressure, ambient gas species, etc.), and often little can be said about them that is truly generic. We shall not attempt to model these terms in the simple generalized discussion presented here.

We can, however, make some concrete statements about the readout's contribution. We write $S_f^{(RO)} = S_V/(\partial V/\partial \omega)^2$ where $S_V$ is the spectral density of voltage noise at the output of the resonator's displacement transducer and $(\partial V/\partial \omega)$ is the rate of change of the transducer output in the vicinity of the resonance frequency. We can crudely approximate the latter as.

$$(\partial V/\partial \omega) \sim \frac{V_{max}}{\Delta \omega} = \frac{QV_{max}}{\omega_0} \quad [6]$$

Here $V_{max}$ is the maximal response of the transducer (on resonance).

In general, we perform mass sensing by driving the resonator, and looking for a frequency shift in steady-state. Hence $V_{max}$ implicitly depends upon the drive level, and to maximize the signal-to-noise ratio (SNR) one wishes to apply the largest drive level tolerable. For the sake of concreteness, we assume that this is the maximum r.m.s. level, $\langle x_{max} \rangle$, still consistent with producing predominantly linear response. For both uniform and point loading of a doubly clamped beam, this can be approximated as $\langle x_{max} \rangle \sim 0.53\,t$, which depends only upon the beam thickness $t$ in the direction of vibration. This, combined with the readout transducer responsivity, $R_T$, (with units volts/meter), enables us to arrive at an expression for the maximum value of $(\partial V/\partial \omega)$ expected:

$$(\partial V/\partial \omega)_{max} \sim \frac{QR_T \langle x_N \rangle}{\omega_0} \sim \frac{0.53 Q R_T t}{\omega_0} \quad [7]$$

Thus, if we consider only the role of readout noise in determining the minimum resolvable frequency shift we obtain the estimate $$\delta \omega_0 \sim [S_f^{(RO)} \Delta f]^{\frac{1}{2}} \sim \frac{\omega_0}{QR_T \langle x_N \rangle}\left[S_V \frac{2\pi}{\tau}\right]^{\frac{1}{2}} \quad [8]$$

Note that this depends inversely upon the ratio of the transducer's maximum response to its noise floor (at the output), $R_T \langle x_N \rangle / [2\pi S_V/T]^{1/2}$. Since this ratio defines the dynamic range (DR) of the coupled mechanical resonator/transducer system, we can write $$\delta \omega_0 \sim \frac{\omega_0}{Q} 10^{-\frac{DR}{20}}.$$

Note that the bandwidth chosen will affect DR.

We can now write a simple expression for the mass sensitivity that is valid in the limit $S_f^i \ll S_f^{(RO)}$ and hence the system noise is dominated by the readout, $$\delta M \sim \frac{\beta}{\alpha^2} \frac{M_{tot}}{Q} 10^{-(DR/20)} \quad [9]$$

With this expression we first estimate the mass sensitivity attainable for our 32.8 MHz device. The relevant parameters for the system built using this SiC device are Q~3000, DR~60 dB for a 3 kHz bandwidth (T ~2 ms), and $M_{tot}$ ~8×10$^{-12}$ g. This leads to the approximate result that $\delta M$ should be a few attograms (10$^{-18}$ g), i.e. ~10$^6$ Da, close to what is experimentally attained.

This agreement gives us confidence to extrapolate to the sensitivity we expect should be attainable in the near term with further optimization of NEMS devices. Using a 200 MHz resonator with dimensions (w, t, l) of 0.1×0.05×1.4 μm, and $M_{tot}$ ~2×10$^{-14}$, assuming Q~2×10$^4$ and DR~60 dB, one obtains 1.6×10$^{-20}$ g. Our longer-term goal is a 850 MHz resonator, with dimensions 0.02×0.01×0.3 μm, and $M_{tot}$ ~2×10$^{-16}$. Assuming that advances can be made to yield a slightly improved Q~10$^5$ and DR~80 dB at this frequency, one obtains 1.6×10$^{-24}$ g (1 Da). This would yield true atomic resolution, for a single adsorbed species, which need not be charged to be detected.

Figure 6:
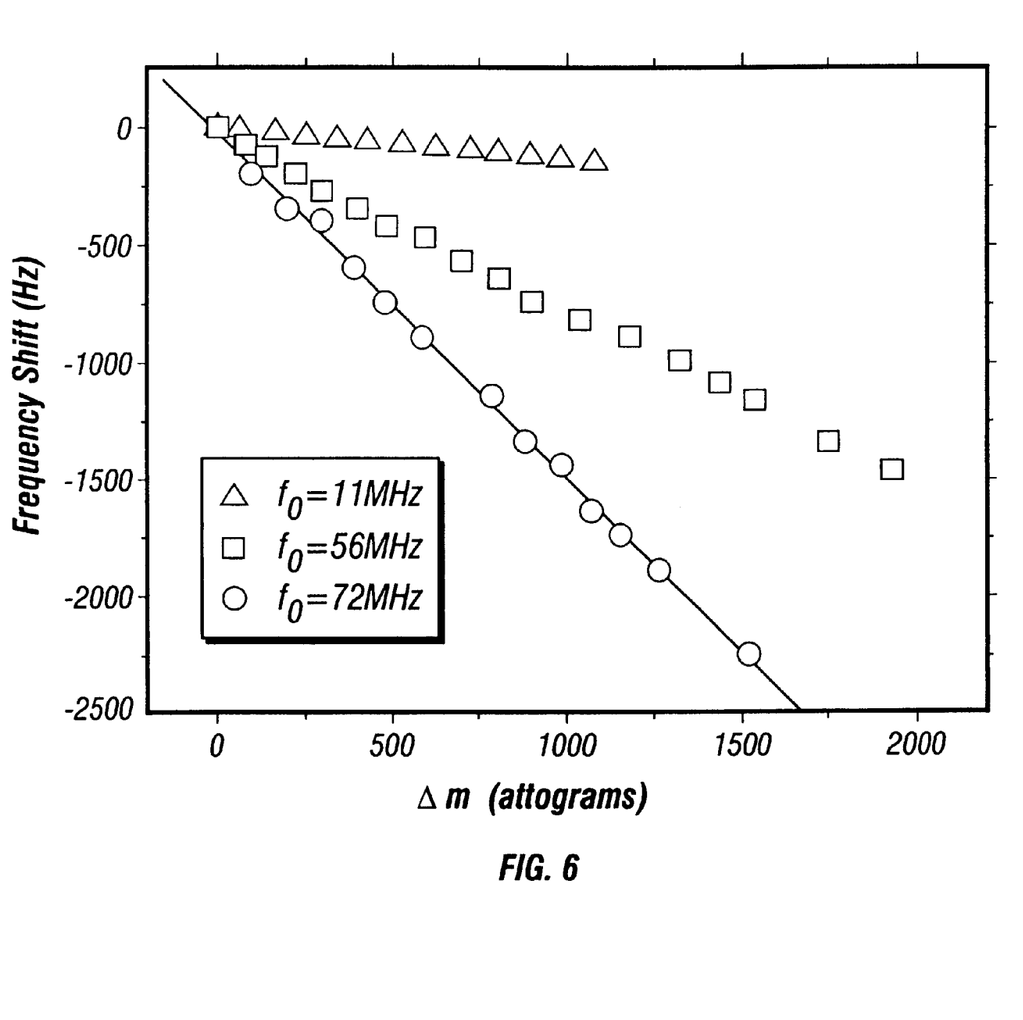
FIG. 6 is a graph of the frequency shift curves for three additional devices with different fundamental frequencies as a function of the added mass, Δm.

Finally, we have repeated our measurements on several devices spanning a range of frequencies and vibratory mass values to demonstrate experimenatally attainable sensitivities. In these measurements, we extract the resonance frequency from experimentally obtained resonance line while the total resonator mass is changed by controlled, sequential pulses of Au deposition. The results are displayed in FIG. 6 and we summarize the estimated and experimental mass responsivity for these resonators in Table I. The estimates are based upon determination of the total resonator masses through direct measurement of their dimensions via electron microscopy. The inverse mass responsivity, is then estimated from the relation $\partial M_{eff}/\partial \omega_0 \cong -1.47 M_{tot}/\omega_0$. FIG. 6 is a graph of the frequency shift curves for three additional devices with different fundamental frequencies as a function of the added mass, $\Delta m$. Each point corresponds to one deposition cycle. Table 1 below shows the parameters for these devices, and the predicted slopes, which are the inverse mass responsivities. The slope for the 72 MHz device corresponds to an experimental inverse mass responsivity of ~51.5 kDa/Hz (80 zg/Hz, where 1 zg=10$^{-21}$ g).

TABLE 1

| $f_0 = \omega_0/2\pi$ (MHz) | L × w × t (μm) | $M_{tot}$ (pg) | Estimated $2\pi \frac{\partial M_{eff}}{\partial \omega_0}$ (Da/Hz) | Experimental $2\pi \frac{\partial M_{eff}}{\partial \omega_0}$ (Da/Hz) |
|---|---|---|---|---|
| 11.4 | 0.8 × 0.259 × 26.2 | 36 | 2.8 MDa/Hz | 1.2 MDa/Hz |
| 32.8 | 0.67 × 0.259 × 14.2 | 8.7 | 235 kDa/Hz | 165 kDa/Hz |
| 56 | 0.65 × 0.259 × 12 | 7.1 | 115 kDa/Hz | 118 kDa/Hz |
| 72 | 0.65 × 0.259 × 10 | 6.0 | 73.5 kDa/Hz | 51.5 kDa/Hz |

These results clearly indicate the immense potential for NEMS-based mass spectrometry (NEMS-MS). Time-of-flight mass spectrometry (TOF-MS), the current mainstay in this field, is restricted to analysis of ionized species in the gas phase. In TOF-MS, gas phase ions are typically first created by a desorption/ionization technique such as plasma desorption (PD) or laser desorption (LD) and, subsequently, accelerated by an electric and/or magnetic field and directed into a drift tube. A detector ultimately records the time of flight of the ions within this tube, which depends on their m/Z ratios. An inherent, and important, limitation of this method is that the absolute mass itself is not accessible, but instead it is the ratio m/Z that is obtained. The mass resolution, m/Δm is determined by the spread in the initial distribution of the velocities of the ions upon desorption. This causes their arrival time, t at the detector, to involve a temporal uncertainty which can be characterized by its average magnitude Δt; hence m/Δm~t/Δt. The best current TOF-MS systems have resolving power of order m/Δm~10$^4$ to 10$^5$ for large molecules (M~10–100 kDa). Further limitations are also imposed upon the size of molecules that can be handled with TOF-MS due to the need to ionize the analytes. Since the ionization energies are generally rather substantial, large molecules may fragment during such ionization. Moreover, the detection of such macromolecules constitutes a major challenge given that the efficiency of conventional particle detectors decreases rapidly with increasing mass. State-of-the-art cryogenic particle detectors cooled to temperatures approaching 100 mK have recently extended the range of MS up to the ~1–10 MDa regime. An additional complication for ionization-based techniques is that they can be inefficient; often much of the analyzed material ends up electrically-neutral, and hence, undetectable. The amount of minimum sample material for a conclusive mass measurement, often referred to as the sensitivity of the MS, and can thus be rather appreciable.

With attainment of single Dalton mass resolution, NEMS-MS will offer immense promise for mass spectrometry of individual macromolecules. In one possible implementation, a very low flux beam of neutral, gas phase species of the sample would impinge and adhere to a NEMS resonator. Individually resolved jumps in the resonance frequency of the NEMS device would directly indicate the mass of these adsorbing molecules. This approach offers the unique capability of mass spectrometry of individual neutral species. After a series of such measurements, the system could be regenerated by thermal desorption of the adsorbates.

Even before single-Dalton resolution is attained, NEMS devices can provide significant enhancement of conventional mass spectrometry if employed as detectors for conventional TOF-MS. In such an implementation, with a NEMS resonator to detect single ion adsorption events, an arbitrarily large mass resolution would be achievable through signal averaging. Here, for ease of discussion, we describe the resolution improvement for a single component analyte in a matrix such in the MDa range. The "frequency dynamic range" of NEMS-MS is exceptionally large, and to a significant degree, essentially independent of the mass sensitivity, $\delta M$, that is determined by random frequency fluctuation processes. If the mass sensitivity is equal to, or better than the analyte mass, m, it becomes possible to count, individually, a large number, N>>1, of single molecule adsorption events, and to ultimately attain an effective mass resolution of, roughly, $m/\Delta m \sim m(N/\delta M)$. With the ~1 MDa sensitivity demonstrated here, with sequential deposition of $N \sim 10^6$ individual 1 MDa species it will be possible to obtain a single Dalton resolution for this hybrid NEMS/TOF-MS. Apparently the resolving power in such a measurement will increase in direct proportion to the measured mass, unlike the case for conventional MS approaches. With NEMS detection, the minimum temporal separation between individual molecular sensing events is determined by the averaging time required to determine the instantaneous frequency to the desired measurement accuracy. For our 32.8 MHz experiment, the 2 ms averaging time would yield ~1 Da sensitivity for ~1 MDa species ($m/\Delta m \sim 10^6$) in ~30 m. During this time the resonance frequency would shift by only ~6.5 MHz. We have investigated the degradation in mass sensitivity of a NEMS resonator as it becomes heavily mass loaded. With sufficient adsorbed material (Pb) to shift the frequency of an (initially) ~38.2 MHz resonator by ~5 MHz, the Q was decreased by only a factor of order ~10%. This immense "mass dynamic range" is one of the important attributes of the NEMS technique.

In summary, even the simplest initial realizations of NEMS-MS described here appear to offer immense advances to the current state-of-the-art. Most notable are the significant increase in sensitivity, and the possibility of mass spectrometry of fragile molecules that are difficult to ionize non-destructively. NEMS-MS is unique in that it yields the absolute mass, rather than the m/Z ratio of an ion, and yields exceptionally large dynamic range for mass measurements. Additional advances in NEMS that appear to be realizable in the near term make feasible single-molecule NEMS-MS with 1 Da resolution. offering the exciting prospect of, in effect, "weighing" individual molecules.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus for measuring microscopic magnitudes of mass comprising:
    a nanoelectromechanical resonator arranged and configured in a vacuum to receive added mass to a vibrating element included within the resonator; and
    an electronic circuit to drive the resonator and to measure a mechanical resonance frequency of the resonator, whereby changes in the frequency of oscillation of the resonator indicate the magnitude of mass added to the vibrating element.

2. The apparatus of claim 1 further comprising a vacuum chamber for providing the vacuum enclosing the nanoelectromechanical resonator.

3. The apparatus of claim 1 wherein the added mass is of the order of one or more macromolecules of matter adsorbed onto the vibrating element.

4. The apparatus of claim 1 wherein the vibrating element comprises a doubly clamped SiC beam.

5. The apparatus of claim 1 wherein the vibrating element comprises a VHF nanoelectromechanical element.

6. The apparatus of claim 1 further comprising a plurality of baffles to shield the nanoelectromechanical resonator from radiation.

7. The apparatus of claim 2 further comprising a plurality of baffles to shield the nanoelectromechanical resonator from radiation.

8. The apparatus of claim 1 further comprising means for thermally shielding the nanoelectromechanical resonator.

9. The apparatus of claim 1 further comprising means for thermally stabilizing the nanoelectromechanical resonator.

10. The apparatus of claim 9 where the means for thermally stabilizing the nanoelectromechanical resonator comprises a cryogenic bath surrounding the nanoelectromechanical resonator and thermally coupled thereto.

11. The apparatus of claim 1 wherein $$\delta M \sim C \frac{M_{tot}}{Q} 10^{-(DR/20)},$$

where $\delta M$ is the minimal magnitude of mass measurable by the nanoelectromechanical resonator, C is a constant determined by the geometry of the vibrating element, $M_{tot}$ is the total mass of the vibrating element, Q is the resonant quality factor of the nanoelectromechanical resonator, and DR is the dynamic range of the nanoelectromechanical resonator.

12. The apparatus of claim 1 wherein the added mass consists substantially of uncharged matter adsorbed to the vibrating element.

13. A method for measuring microscopic magnitudes of mass comprising the steps of:
providing a nanoelectromechanical resonator arranged and configured to receive added mass to a vibrating element included with the resonator, an electronic circuit to drive the resonator and to measure a frequency of oscillation of the resonator;
enclosing the nanoelectromechanical resonator in a vacuum chamber;
driving the vibrating element with the circuit to establish a steady state resonant frequency;
adsorbing mass onto the vibrating element; and
sensing the change of the steady state resonant frequency as a direct measure of the adsorbed mass,
whereby changes in the frequency of oscillation of the resonator indicate the magnitude of mass added to the vibrating element.

14. The method of claim 13 where in the step of adsorbing mass onto the vibrating element the added mass is of the order of one or more macromolecules of matter.

15. The method of claim 13 where in the step of driving the vibrating element with the oscillator the vibrating element comprises a doubly clamped SiC beam.

16. The method of claim 13 where in the step of driving the vibrating element with the oscillator the vibrating element comprises a VHF nanoelectromechanical element.

17. The method of claim 13 further comprising the step of shielding the nanoelectromechanical resonator from radiation.

18. The method of claim 13 further comprising the step of shielding the nanoelectromechanical resonator from radiation with a plurality of baffles.

19. The method of claim 13 further comprising the step of thermally shielding the nanoelectromechanical resonator.

20. The method of claim 13 further comprising the step of thermally stabilizing the nanoelectromechanical resonator.

21. The method of claim 20 where the step of thermally stabilizing the nanoelectromechanical resonator comprises the step of surrounding the nanoelectromechanical resonator with a cryogenic bath and thermally coupling the nanoelectromechanical resonator thereto.

22. The method of claim 13 wherein the step of sensing the change of the steady state resonant frequency as a direct measure of the adsorbed mass senses at least the added mass, $$\delta M \sim C \frac{M_{tot}}{Q} 10^{-(DR/20)},$$

where $\delta M$ is the minimal magnitude of mass measurable by the nanoelectromechanical resonator, C is a constant determined by the geometry of the vibrating element, $M_{tot}$ is the total mass of the vibrating element, Q is the resonant quality factor of the nanoelectromechanical resonator, and DR is the dynamic range of the nanoelectromechanical resonator.

23. The method of claim 13 wherein the step of sensing the change of the steady state resonant frequency as a direct measure of the adsorbed mass senses the added mass, which consists substantially of uncharged matter adsorbed to the vibrating element.

24. The method of claim 13 further comprising the step of regenerating the nanoelectromechanical resonator by desorbing the added mass from the vibrating element.

25. The method of claim 13 further comprising the step of performing a time-of-flight mass spectrometry measurement in which the steps of driving, adsorbing and sensing are used collectively as a detecting step in the time-of-flight mass spectrometry measurement.

* * * * *